US011903925B2

(12) United States Patent
Uttenthal

(10) Patent No.: US 11,903,925 B2
(45) Date of Patent: Feb. 20, 2024

(54) COMPOSITIONS FOR PREVENTING AND TREATING PULMONARY INJURY DUE TO IONIZING RADIATION OR CYTOTOXIC DRUGS

(71) Applicant: RepoCeuticals A/S, Hørsholm (DK)

(72) Inventor: Lars Otto Uttenthal, Madrid (ES)

(73) Assignee: RepoCeuticals A/S, Hørsholm (DK)

( * ) Notice: Subject to any disclaimer, the term of this patent is extended or adjusted under 35 U.S.C. 154(b) by 0 days.

(21) Appl. No.: 16/162,222

(22) Filed: Oct. 16, 2018

(65) Prior Publication Data

US 2019/0282545 A1 Sep. 19, 2019

Related U.S. Application Data

(62) Division of application No. 15/543,545, filed as application No. PCT/EP2016/052195 on Feb. 2, 2016, now abandoned.

(30) Foreign Application Priority Data

Feb. 2, 2015 (DK) .............................. PA201570059

(51) Int. Cl.
*A61K 31/4045* (2006.01)
*A61K 31/122* (2006.01)
*A61K 31/355* (2006.01)
*A61K 31/375* (2006.01)
*A61K 31/385* (2006.01)
*A61K 9/00* (2006.01)

(52) U.S. Cl.
CPC ........ *A61K 31/4045* (2013.01); *A61K 9/0073* (2013.01); *A61K 31/122* (2013.01); *A61K 31/355* (2013.01); *A61K 31/375* (2013.01); *A61K 31/385* (2013.01)

(58) Field of Classification Search
None
See application file for complete search history.

(56) References Cited

U.S. PATENT DOCUMENTS

2002/0048551 A1  4/2002  Keller et al.
2013/0210758 A1*  8/2013  Keller ................... A61M 15/06
                                              514/52
2016/0045434 A1*  2/2016  Caponetti .............. A61K 47/26
                                              514/174

FOREIGN PATENT DOCUMENTS

WO  WO2014089174  6/2014

OTHER PUBLICATIONS

Gaksel Sener et al: "Melatonin ameliorates ionizing radiation-induced oxidative organ damage in rats.", Life Sciences, vol. 74, No. 5, Dec. 1, 2003 (Dec. 1, 2003), pp. 563-572 (Year: 2003).*

Database Biosis [Online] Biosciences Information Service, Philadelphia, PA, US; Mar. 2007 (Mar. 2007), Serin Meltem et al: International Journal of Radiation Biology, vol. 83, No. 3, Mar. 2007 (Mar. 2007), pp. 187-193 (Year: 2007).*
Zhen-Hua Wu:Space Medicine & Medical Engineering» 20102 ;, Apr. 1, 2010 (Apr. 1, 2010), p. 95, XP055255029, Retrieved from the Internet: URL:http://en.cnki.com.cn/Article_en/CJFDTOTAL-HYXB201002003.htm [retrieved on Mar. 3, 2016]; (Year: 2016).*
Database Biosis [Online] Biosciences Information Service, Philadelphia, PA, US; Feb. 2013 (Feb. 2013), Jang Seong Soon et al: International Journal of Radiation Biology, vol. 89, No. 2, Feb. 2013 (Feb. 2013), pp. 97-105 (Year: 201).*
Database Biosis [Online] Biosciences Information Service, Philadelphia, PA, US; Sep. 2005 (Sep. 2005), Genovese Tiziana Et A, Journal of Pineal Research, vol. 39, No. 2, Sep. 2005 (Sep. 2005), pp. 105-112 (Year: 2005).*
Eser Oz et al: "Effects of melatonin in reducing the toxic effects of doxorubicin", Molecular and Cellular Biochemistry, Kluwer Academic Publishers, BO, vol. 286, No. 1-2, Apr. 20, 2006 (Apr. 20, 2006), pp. 11-15 (Year: 2006).*
Ucar et al: "Melatonin alleviates lung damage induced by the chemical warfare agent nitrogen mustard", Toxicology Letters, Elsevier Biomedical Press, Amsterdam, NL, vol. 173, No. 2, Sep. 5, 2007 (Sep. 5, 2007), pp. 124-131 (Year: 2007).*
Alexanderv Siprov et al, Russian Open Medical Journal, Jan. 1, 2013 (Jan. 1, 2013), pp. 2304-3415906, XP055255041, Retrieved from the Internet: URL:http://www.romj.org/files/pdf/romj-2013-0304.pdf [retrieved on Mar. 3, 2016] (Year: 2013).*
M. V. Vasin et al: "Therapeutic Effect of Long-Term Melatonin Treatment on theCourse and Fatal Outcome of Modeled Acute Radiation Sickness", Bulletin of Experimental Biology and Medicine, vol. 156, No. 6, Apr. 1, 2014 (Apr. 1, 2014), (Year: 2014).*
Priprem et al., Open Access Scientific Reports, vol. 1, Issue 4, 2012 (Year: 2012).*
Schaffazick et al., J. Braz. Chem. Soc., vol. 17, No. 3, 562-569, 2006 (Year: 2006).*
Meltem et al., "The histopathological evaluation of the effectiveness of melatonin as a protectant against acute lung injury induced by radiation therapy in a rat model", XP002755084, Database BIOSIS [Online] Biosciences Information Service, 2007; Database accession No. PREV200700215812; & International Journal of Radiation Biology, 83 (3): 187-193.
Öz et al., "Effects of melatonin in reducing the toxic effects of doxorubicin", Molecular and Cellular Biochemistry, 2006, 286: 11-15.
Sener et al., "Melatonin ameliorates ionizing radiation-induced oxidative organ damage in rats", Life Sciences, 2003, 74:(5): 563-572.
Siprov et al., "Comparative evaluation of antioxidant drug influence on a radio therapy efficiency and oxidative status in mice", Russian Open Medical Journal, 2013, 2: 0304.

(Continued)

*Primary Examiner* — Karl J Puttlitz
(74) *Attorney, Agent, or Firm* — Knobbe Martens Olson Bear LLP

(57) ABSTRACT

Compositions comprising melatonin or derivatives thereof for administration to the epithelium of the lower airway to protect against lung damage due to chest irradiation and/or cytotoxic chemotherapy are provided.

8 Claims, No Drawings

(56) References Cited

OTHER PUBLICATIONS

Soon et al., "Melatonin reduces X-ray radiation-induced lung injury in mice by modulating oxidative stress and cytokine expression", XP002755085, Database BIOSIS [Online] Biosciences Information Service, 2013, Database accession No. PREV201300219958; & International Journal of Radiation Biology, 89(2): 97-105.

Tiziana et al., "Melatonin limits lung injury in bleomycin treated mice", XP002755085, Database BIOSIS [Online] Biosciences Information Service, 2005, Database accession No. PREV200510282091; & Journal of Pineal Research, 39(2):105-112.

Ucar et al., "Melatonin alleviates lung damage induced by the chemical warfare agent nitrogen mustard", Toxicology Letters, Elsevier Biomedical Press, 2007, 173(2): 124-131.

Vasin et al., "Therapeutic Effect of Long-Term Melatonin Treatment on the Course and Fatal Outcome of Modeled Acute Radiation Sickness", Bulletin of Experimental Biology and Medicine, 2014, 156(6):0776-777.

Wu et al., "Study on Protective Effect of Melatonin against Radiation Damages of Lung in Mice Induced by Heavy Ion Beams", Space Medicine & Medical Engineering, 2010, p. 95, URL:http://en.cnki.com.cn/Article_en/CJFDTOTAL-HYXB201002003.HYM.

Lipoceutical Melatonin Spray, at URL: https://www.vitacost.com/natures-plus-melatonin-lipoceutical-spray#BVRRWidgetID, visited by examiner Karl J. Puttlitz on Nov. 20, 2017.

\* cited by examiner

COMPOSITIONS FOR PREVENTING AND TREATING PULMONARY INJURY DUE TO IONIZING RADIATION OR CYTOTOXIC DRUGS

CROSS-REFERENCING

This application is a divisional of U.S. application Ser. No. 15/543,545, filed on Jul. 13, 2017, which is the national phase under 35 U.S.C. § 371 of International Application No. PCT/EP2016/052195, filed on Feb. 2, 2016, which claims benefit of priority to Danish Application No. PA201570059, filed on Feb. 2, 2015, which applications are incorporated by reference herein.

FIELD OF INVENTION

The present invention provides compositions comprising melatonin or a derivative thereof as the essential ingredient for preventing and treating pulmonary injury due to ionizing radiation or cytotoxic drugs by inhalation or other form of airway administration. As such, it is particularly relevant to the fields of oncology, radiotherapy and respiratory or chest medicine.

BACKGROUND OF THE INVENTION

Pulmonary Radiation Injury

Pulmonary radiation injury, in the form of symptomatic radiation pneumonitis (pulmonary inflammation), is estimated to affect about 7% of all patients receiving radiotherapy to the chest, while over 40% of patients may show radiological changes of injury (Movsas et al 1997). Radiotherapy to the chest is most commonly given in cases of breast and lung cancer and in Hodgkin's disease.

Radiation Pneumonitis:

Pulmonary radiation injury is particularly associated with radiation doses above about 2 Gy. Free radicals are produced in the cells which exceed the cells' intrinsic scavenging capabilities and airway epithelial cells may die. Because of their higher mitotic turnover rate, type II (or granular) pneumocytes, which are the principal source of surfactant, are particularly affected. In animal experiments, electron microscopic changes are seen in these cells within 1 hour of irradiation, with early release and depletion of surfactant, which is essential for maintaining the alveolar patency. By 24 hours, the surfactant-containing lamellar bodies are depleted and there is sub-endothelial and perivascular edema. Then follows inflammatory changes in which the alveolar septa are infiltrated by mast cells, plasma cells, fibroblasts, macrophages and polymorphonuclear cells, and show incipient interstitial fibrosis. Small airways and blood vessels may be occluded. Clinically, these early changes of pulmonary radiation injury, known as radiation pneumonitis, become evident about 4-12 weeks after a course of radiotherapy. Clinical symptoms will typically be shortness of breath, cough, and chest discomfort, with increased susceptibility to lung infections, which may be lethal. The damaging process may cease while the patient still retains enough pulmonary function to maintain life, or may progress to cause acute respiratory distress syndrome and eventual death from pulmonary fibrosis.

Radiation Fibrosis:

The changes of radiation pneumonitis are followed by the longer-term development of pulmonary fibrosis, which may, however, also occur without a history of preceding radiation pneumonitis. The permanent changes of radiation fibrosis take 6 to 24 months to evolve, but usually remain stable after 2 years. The initiation of fibrosis is already seen in radiation pneumonitis, but further fibrosis takes place under the influence of a cascade of inflammatory cytokines and growth factors released from injured type II pneumocytes and alveolar macrophages that stimulate fibroblast proliferation and induce the synthesis and secretion of collagen and fibronectin. Both transforming growth factor beta (TGF-beta) and tumor necrosis factor alpha (TNF-alpha) have been implicated. Patients may present with varying degrees of shortness of breath. If a large volume of lung has been irradiated, chronic pulmonary insufficiency may develop, which may lead to pulmonary hypertension and cor pulmonale.

With high radiation doses (e.g. 20 Gy or more), as may be seen in nuclear incidents, the time course of pulmonary radiation damage may be shortened and initial symptoms of radiation pneumonitis appear within a few days.

Pulmonary Injury Due to Cytotoxic Drugs

A similar type of lung damage may be seen with the use of cytotoxic chemotherapeutic agents for cancer. Bleomycin is the agent which is most commonly involved and the best studied, but other cytotoxic agents may also damage the lung, such as mitomycin C, bis-chloroethylnitrosourea (BCNU or carmustine), cyclophosphamide, busulfan, methotrexate, doxorubicin, gemcitabine, paclitaxel, docetaxel and carboplatin. Bleomycin and many of the other agents initiate lung damage by their intracellular oxidizing properties, producing reactive oxygen species (ROS) exceeding the free radical scavenging capacity of the cells and inducing cell death. This is also part of their cytotoxic anti-tumor action. As might be expected, the risk of pulmonary toxicity is augmented by raising the fraction of inspired oxygen. This also applies to mitomycin C, cyclophosphamide and busulfan, suggesting that their toxicity is also initiated by ROS.

In this respect, the pathology of lung damage due to these cytotoxic agents is very similar to that of radiation injury, and the subsequent evolution of pneumonitis and pulmonary fibrosis follows a similar sequence, the time course being shortened or extended depending on the type of drug and dosage. Methotrexate characteristically causes hypersensitivity-induced inflammatory lung damage in the form of a pneumonitis, which, however, only rarely progresses to pulmonary fibrosis. The overall rate of pulmonary damage due to these agents varies from less than 1% for methotrexate and cyclophosphamide to over 40% for bleomycin. The mortality varies from 10% to over 83%.

Pulmonary Injury Due to a Combination of Radiotherapy and Cytotoxic Drugs

Many of the above-mentioned drugs and other antineoplastic agents that by themselves only rarely cause pulmonary injury potentiate the damaging effects of pulmonary radiation. Thus, bleomycin given together with radiotherapy to the chest produces greater pulmonary injury than either treatment administered alone. Cyclophosphamide and doxorubicin also enhance the toxicity of thoracic irradiation. The additive or synergic effect of chemotherapy and chest irradiation to cause lung damage is especially marked when the treatments are administered concurrently rather than sequentially.

Current Treatment of Pulmonary Injury Due to Radiation and/or Cytotoxic Drugs

The onset of pulmonary injury during radiotherapy and/or cytotoxic chemotherapy is potentially limiting to the anti-cancer treatment in terms of duration and dosage. It is therefore important to try to minimize the lung damage. The main treatment strategy has been to suppress the inflammatory response to the radiation or cytotoxic cellular injury that subsequently contributes to the pathological process. The most commonly used anti-inflammatory therapy has been immunosuppression with prednisone at 1 mg/kg/day for several weeks before tapering off the dosage. This carries with it the considerable disadvantage of generalized immunosuppression and the other adverse effects of glucocorticoid treatment in the form of Cushing's syndrome. Azathioprine and cyclosporin A have also been tried as immunosuppressive agents in this context, in order to avoid the Cushingoid side effects of prednisone. Non-steroid anti-inflammatory agents have also been tried, but with insufficient effect. Symptomatic treatments with decongestants, cough suppressants and bronchodilators are regularly used, but have no effect on the underlying pathology. There is a medical need for a preventive or pre-emotive treatment of radiation and cytotoxic lung injury that treats the root intracellular cause of the pathological process without incurring the considerable disadvantages and danger to the patient of generalized immunosuppression.

Melatonin

Melatonin (N-acetyl-5-methoxytryptamine) is a hormone produced by the pineal gland in human beings and other mammals by enzymatic modification of the amino acid tryptophan. Melatonin is involved in maintaining the circadian rhythm of various biological functions, being secreted in hours of darkness and acting on high-affinity melatonin $G_i$-coupled transmembrane receptors MT1 and MT2, which are widely distributed in many cells and tissues of the body. At the same time melatonin acts at supraphysiological concentrations as a powerful antioxidant and free radical scavenger for ROS and reactive nitrogen species (Gomez-Moreno et al 2010). Melatonin can also activate cytoprotective antioxidative enzymes such as copper-zinc and manganese superoxide dismutases (CuZnSOD and MnSOD) and glutathione peroxidase (Rodriguez et al 2004). Melatonin also has anti-inflammatory effects to prevent the upregulation or cause the down-regulation of the expression of nuclear factor kappa B (NF-κB) and pro-inflammatory cytokines such as tumor necrosis factor alpha (TNF-α) and interleukin 1 beta (IL-1β).

Melatonin as an Agent to Protect Against Radiation Injury:

Because of melatonin's efficiency as a free radical scavenger, especially of hydroxyl radicals (Tan et al 1993) and ROS, it has been proposed as an agent to protect against radiation injury to cells and tissues. The protective effect of high dose systemic melatonin against the harmful effects of whole-body irradiation has been studied chiefly in rodents. Melatonin has typically been given at intravenous or intraperitoneal doses of 5 mg to 100 mg per kilogram of body weight and protective effects on DNA and nuclear morphology, as well as prolonged survival after lethal doses of irradiation have been observed. Melatonin has been demonstrated to protect against the adverse effects of all relevant wavelengths ionizing radiation from ultraviolet through x-rays to gamma rays. The results of such studies have been reviewed by Vijayalaxmi et al (2004). In human beings, a protective effect of prior oral melatonin dosage on the damage caused by subsequent ex vivo radiation exposure of lymphocytes has been observed (Vijayalaxmi et al 1996). However, controlled clinical trials of the protective effect of oral or systemic melatonin on radiation damage in patients undergoing radiotherapy are lacking.

The above experiments suggest that a major part of the protective effect of melatonin against radiation damage depends on the intracellular presence of melatonin at the time of radiation. This would be consistent with the near instantaneous intracellular production of free radicals as a result of radiation and their initiation of DNA and mitochondrial damage leading to cell death. There has been some concern that pre-treatment with systemically administered melatonin would also diminish the effectiveness of radiotherapy to kill tumor cells. However, the effects of melatonin to activate cytoprotective enzymes and down-regulate pro-inflammatory cytokines points to a longer term effect that might contribute to protection against radiation damage.

Melatonin Metabolites, Derivatives and Analogues

Many chemical derivatives of melatonin, including breakdown products and natural metabolites of melatonin, retain the antioxidant and free-radical scavenging properties of the parent molecule. This makes melatonin a more effective antioxidant than other natural antioxidants such as vitamins C and E (cited by Reiter et al 2007). However, these vitamins show synergy with melatonin with respect to antioxidant activity. In non-hepatic tissues, the reaction of melatonin with two hydroxyl radicals yields the metabolite cyclic 3-hydroxymelatonin (C3-OHM), which undergoes further oxidation by two hydroxyl radicals to break the indole ring and form $N^1$-acetyl-$N^2$-formyl-5-methoxykynuramine (AFMK) (Tan et al 1993; Reiter et al 2007). C3-OHM is therefore also an effective antioxidant and hydroxyl radical scavenger. The reaction of melatonin with the hydroxyl radical precursor, hydrogen peroxide, similarly leads to production of AFMK. AFMK is also a reducing agent, capable of donating electrons to detoxify radical species, and has been shown to preserve the integrity DNA exposed to oxidizing agents. The action of aryl formamidase or catalase on AFMK produces $N^1$-acetyl-5-methoxykynuramine (AMK), which is an even more effective scavenger of hydroxyl radicals and reactive nitrogen species, protecting proteins from oxidative destruction. In this process, 3-acetamidomethyl-6-methoxycinnolinone (AMMO) or 3-nitro-AMK (AMNK) are formed.

The liver is the principal site of the classically reported metabolic pathway for melatonin. This consists chiefly of 6-hydroxylation by the cytochromes P450 CYP1A1, CYP1A2, and CYP1B1, and the formation of the minor metabolite N-acetylserotonin by CYP2C19. The main product 6-hydroxymelatonin (6-OHM) is then conjugated at the hydroxyl group to form the 6-OHM glucuronide or 6-OHM sulfate. 6-OHM is an effective free radical scavenger in a variety of situations, but is also reported to show pro-oxidant effects in others. Its status as an antioxidant thus remains equivocal (Maharaj et al 2007).

N-acetylserotonin (NAS) is not only the immediate biosynthetic precursor but also a minor metabolite of melatonin. Like 6-OHM, it is conjugated to form the glucuronide or sulfate. Its protective effect against oxidative damage in certain model systems is reportedly 5 to 20 times as strong as that of melatonin (Oxenkrug 2005).

Melatonin can also be chemically modified by introducing chemical groups at one or more of any of its constituent atoms susceptible of such modification or by introducing such groups in de novo synthesis of melatonin analogues or derivatives. Such modifications, which do not alter the fundamental indole structure of melatonin, are herein called derivatives. The fundamental indole structure of melatonin can also be modified by substituting other bicyclic aromatic structures. Such modifications are herein called analogues, which may also have different chemical side groups removed, introduced or modified. Many such analogues and derivatives have been prepared, but most of them have not been tested for their antioxidant or free-radical scavenging properties.

Natural Antioxidants that May Act in Synergy with Melatonin

A large number of natural antioxidant agents that have been used pharmaceutically may potentially act synergically with melatonin. These are known to the skilled person and may have additive antioxidant effects, but only a few have been demonstrated to act synergically. Vitamins C and E have been cited in this context. A related but not identical property, which is less well assessed, is their efficiency as free radical scavengers and in conferring protection against the harmful effects of radiation and cytotoxic medication. Further natural antioxidants that come under consideration as conferring addition protective effect are alpha-lipoic acid and coenzyme Q10 (also known as ubidecarenone). Both are effective as free radical scavengers and their capacity to ameliorate radiation damage has been demonstrated in vitro and in animal models in which the substances have usually been given intraperitoneally or by dietary supplementation. There is preliminary evidence that intraperitoneally administered coenzyme Q10 ameliorates radiation pneumonitis is mice (Hashimura et al 1989).

SUMMARY OF THE INVENTION

In view of the above considerations, the invention consists of providing pharmaceutical compositions comprising essentially melatonin or an antioxidant metabolite, derivative or analogue thereof (individually referred to as the protective agent) for the prevention and treatment of pulmonary injury due to radiation and/or cytotoxic drugs by the direct administration of the compositions to the epithelium of the lower airways by the inhalation of the composition or a nebulized solution of the composition or by any other means of direct administration to the lower airways. The advantage of the invention is that the protective agent is delivered at high dosage directly to the tissue for which protection from radiation or cytotoxic damage is desired. A further advantage is that melatonin directly applied to the lower airways will not be subject to the low bioavailability of melatonin given orally, which is subject to individually variable first-pass metabolism in the liver, so that the effective dose given to the lower airways will be predictable. The compositions are intended to be administered immediately before each dose of radiotherapy is given to the chest and at various other times during and after a course of radiotherapy, and immediately before each dose of cytotoxic chemotherapy and at various other times during and after a course of such chemotherapy.

Pharmaceutical compositions are also provided which comprise melatonin or an antioxidant analogue, derivative or metabolite thereof and a pharmaceutically acceptable form of vitamin E and/or coenzyme Q10 and/or alpha-lipoic acid and/or vitamin C.

Accordingly, the pharmaceutical compositions comprise essentially:

A composition comprising melatonin or an antioxidant metabolite, derivative or analogue thereof formulated to be suitable for administration to the epithelium of the lower airways, for example, by the inhalation of the composition or for an aerosol of a solution of the composition, for the prevention and treatment of lung damage due to chest irradiation and/or the administration of cytotoxic drugs; and:

A composition according to that described above, comprising additionally a pharmaceutically acceptable form or derivative or analogue of one or more of the substances vitamin E, coenzyme Q10, alpha-lipoic acid and vitamin C.

The invention fulfills the medical need for a preventive, pre-emptive and continuing treatment of the root intracellular cause of radiation and cytotoxic pulmonary injury without resorting to the generalized immunosuppression that is the mainstay of current treatment and which produces serious and dangerous adverse effects. In the case of cytotoxic chemotherapy, the immunosuppression produced by current treatment is additive to that already caused by the cytotoxic agent(s), making its avoidance even more important.

The invention is also suitable for use in imminent or recent radiation exposure due to a nuclear event such as an attack or accident and for more prolonged exposure to background radiation following such an event.

In the following detailed description of the invention, details of the scope of the invention will be given, together with details of the practical performance of the invention.

DETAILED DESCRIPTION OF THE INVENTION

The present invention provides compositions comprising melatonin or an antioxidant metabolite, derivative or analogue thereof as the active substance to be delivered to the lower airways epithelium via the airways for the prevention and treatment of pulmonary injury due to radiation and/or cytotoxic drugs. It also provides for compositions for the same purpose, which additionally comprise a pharmaceutically acceptable form or derivative or analogue of one or more of the substances vitamin E, coenzyme Q10, alpha-lipoic acid and vitamin C.

Active Ingredients

The principal active ingredient of the compositions of the invention is melatonin or an antioxidant metabolite, derivative or analogue thereof.

Antioxidant Metabolites of Melatonin:

Of those described above, $N^1$-acetyl-$N^2$-formyl-5-methoxykynuramine (AFMK), 6-hydroxymelatonin (6-OHM) and N-acetylserotonin (NAS) can be used in compositions of the invention. Cyclic 3-hydroxymelatonin (C3-OHM) and $N^1$-acetyl-5-methoxykynuramine (AMK) are unstable and hence unsuitable for use in a pharmaceutical composition.

Antioxidant Melatonin Derivatives:

The chemical structure of melatonin can be represented as in Figure (I), in which sites suitable for chemical modification by the substitution of different chemical groups have been indicated by $R_1$, $R_2$, $R_3$, $R_4$, $R_5$ and $R_6$. These numbers do not correspond to the conventional numbering of positions in the indole ring of melatonin.

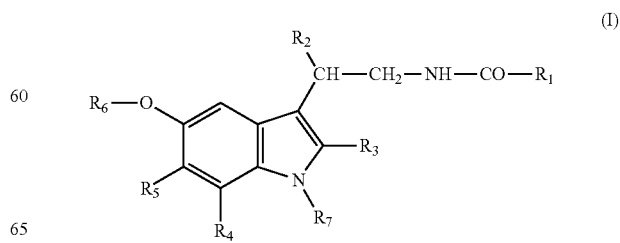

In native melatonin, $R_1$ and $R_6$ represent $CH_3$, while $R_2$, $R_3$, $R_4$, $R_5$ and $R_7$ represent H.

Antioxidant melatonin derivatives may comprise, as non-exclusive examples, those in which $R_1$ represents H, a linear or branched $C_1$-$C_4$ alkyl group or a $C_1$-$C_4$ alkoxy group, $R_2$ represents H or a $C_1$-$C_4$ alkyl group, $R_3$ represents H, a methyl group or a halogen atom, $R_4$ represents H or a halogen atom, $R_5$ represents H or a halogen atom, $R_6$ represents H or a linear or branched $C_1$-$C_4$ alkyl group, $R_7$ represents H, a linear or branched $C_1$-$C_4$ alkyl group, a —C(=O)—O—$R_a$ group or a —C(=O)—N(H)—$R_a$ group wherein $R_a$ is a linear or branched $C_1$-$C_4$ alkyl group, the —$CH_2$—NH—C(=O)—$R_1$ side chain is extended by duplicating, triplicating or quadruplicating the —$CH_2$— group, or pharmaceutically acceptable salts of such derivatives.

Synergically Acting Antioxidants:

The present invention also provides compositions comprising melatonin or an antioxidant analogue or metabolite thereof together with a synergically acting antioxidant such as vitamin E, coenzyme Q10, alpha-lipoic acid or vitamin C as active substances. In their native forms, vitamin E is an oil, coenzyme Q10 is an almost water-insoluble solid of low melting point, and alpha-lipoic acid is a water-insoluble solid organic acid, while vitamin C is a solid organic acid. None of these is suitable for direct airway administration in its native form. These substances must therefore be provided in forms that are pharmaceutically acceptable. A non-limiting example of such a form of vitamin E is D-alpha-tocopheryl succinate, a crystalline powder known to be harmless by inhalation. Coenzyme Q10 or a suitable antioxidant analogue or derivative thereof, non-limiting examples of which are coenzyme Q9, decylubiquinone and idebenone, may be rendered pharmaceutically acceptable by adsorption to a biologically acceptable carrier such as beta-cyclodextrin during the formulation process. Alpha lipoic acid R-(+)-alpha-lipoic acid, also called (R)-thioctic acid, is rendered pharmaceutically acceptable by using its sodium salt, sodium thioctate, which is soluble in water to yield solutions of near-physiological pH. Similarly, a non-limiting example of a pharmaceutically acceptable form of vitamin C is sodium ascorbate.

Formulations

The pharmaceutical composition of the present invention may be in the form of a powder, solution, emulsion, suspension, or micellar, microsphere, microcapsular, nanoparticulate or liposomal preparation. Melatonin and most of its analogues, derivatives and metabolites are only sparingly soluble in water, straightforward attempts at dissolving melatonin in water yielding a maximum melatonin concentration of only 0.1 mg/mL. Higher concentrations of melatonin are needed if aqueous preparations of melatonin are to be administered in a convenient manner, e.g. by the inhalation of an aerosol of the preparation, to the airways epithelium at the concentrations estimated to be necessary to exert a protective action against free radical damage. A method of achieving this is outlined below.

A preferred formulation is to supply the pharmaceutical composition as a dry powder in a vial or capsule to be fitted into an apparatus that allows the dry powder to be inhaled directly into the lower airways. The powder consists of 30% to 70% by weight of melatonin together with 70% to 30% by weight of an excipient such as lactose, mannitol or xylitol, the melatonin and the excipient being co-micronized in e.g. a spiral jet micronizer mill to produce particles of an aerodynamic diameter in the range of 2 μm to 5 μm. The details of this processing are well known to those skilled in the art.

A further formulation is to supply the composition as a dry powder as described above in a capped vial, to be reconstituted as a solution for nebulization by adding a given volume of sterile water from a second vial, to be used within one hour. The water for dissolving the formulation may contain the empirically determined amount of salts and buffering ions to produce a solution of the composition that has a near-physiological pH and osmolarity with reference to plasma to avoid the provocation of cough and bronchoconstriction on inhalation. This means a pH between 7 and 8, preferably 7.4, and an osmolarity in the range of 250-300 mOsm/L, preferably 290 mOsm/L. The dry powder for solution may be prepared by mixing equal volumes of a solution of melatonin in ethanol or dimethyl sulfoxide and an aqueous solution of the sugar excipient, which may be lactose, mannitol or xylitol, and then spray-drying the ingredients to produce particles of median diameter less than 50 μm with over 90% by weight of particles being less than 100 μm in diameter. Small amounts, not exceeding 0.4% by weight, of biocompatible detergents such as sodium deoxycholate or lecithin may be added to the solution before spray-drying. Reconstitution of the spray-dried powder with water makes it possible to achieve aqueous solutions with concentrations of melatonin of 2 mg/mL or more.

The conditions of spray drying can also be adjusted to produce solid particles of a size (2 μm to 5 μm in aerodynamic diameter) that can be used for inhalation as a dry powder without employing the procedure of nebulizing and aqueous solution.

Solutes to be added to the water for dissolving the pharmaceutical composition may include hydrochloric acid, sodium hydroxide and biocompatible buffering agents, non-limiting examples being sodium dihydrogen phosphate and disodium hydrogen phosphate, sodium carbonate and bicarbonate. Tonicity-adjusting agents, such as for example sodium chloride or calcium chloride, may also be added.

Formulations according to the present invention may comprise pharmaceutically acceptable carriers and excipients including microspheres, liposomes, micelles, microcapsules, nanoparticles or the like. In an aqueous suspensions of liposomes containing melatonin, which is a relatively hydrophobic substance, the liposomes are unilamellar and their production is well known to the skilled person.

The stated formulation methods can also be applied to the melatonin metabolites, derivatives and analogues of the invention and to D-alpha-tocopheryl succinate, coenzyme Q10 or its analogues and derivatives. In the case of coenzyme Q10 or its analogues and derivatives, the substance is added to the mixture for spray drying in a water-soluble form complexed with a low-molecular weight dextrin, such as beta-cyclodextrin. Sodium ascorbate is water-soluble and presents no unusual formulation requirement.

Administration

Administration of an effective amount of the pharmaceutical composition is by airways administration to the epithelium of the lower airway, such as by inhalation of the composition in fine powder form or by inhalation of an aerosol of a solution of the composition, or by intratracheal, intrabronchial or bronchoalveolar administration.

Methods of intratracheal, intrabronchial or bronchoalveolar administration include, but are not limited to, spraying, lavage, inhalation, flushing or installation, using as fluid a physiologically acceptable composition in which the pharmaceutical composition has been dissolved. When used herein the terms "intratracheal, intrabronchial or intraalveolar administration" include all forms of such administration whereby the composition is applied into the trachea, the bronchi or the alveoli, whether by the instillation of a solution of the composition, by applying the composition in a powder form, or by allowing the composition to reach the relevant part of the airway by inhalation of the composition as an aerosolized or nebulized solution or suspension or inhaled powder, with or without added stabilizers or other excipients.

Methods of intrabronchial or intraalveolar administration also include bronchoalveolar lavage (BAL) according to methods well known to those skilled in the art, using as a lavage fluid a physiologically acceptable composition in which the composition has been dissolved, or by the direct application of the composition, in solution or suspension or powder form during bronchoscopy. Methods for intratracheal administration include blind tracheal washing with a similar solution of dissolved composition or with a suspension of the composition, or the inhalation of nebulized fluid droplets containing the dissolved composition or a suspension of the composition, obtained by use of any nebulizing apparatus adequate for this purpose.

Preferred methods of administration may include using the following devices:
1. Dry powder inhaler systems (DPI).
2. Pressurized nebulizers using compressed air/oxygen mixture
3. Ultrasonic nebulizers
4. Electronic micropump nebulizers (e.g. Aeroneb Professional Nebulizer)
5. Metered dose inhaler (MDI)

The preferred method of administration is 1. above, in which the apparatus allowing the preparation to be inhaled as a dry, micronized powder may be similar to the Spinhaler®, used for administering other micronized powders to the lower airways.

The aerosol may be delivered by a) facemasks or b) endotracheal tubes in intubated patients during mechanical ventilation (device 1, 2 and 3). The devices 4 and 5 can also be used by the patient without assistance, provided that the patient is able to self-activate the aerosol device.

Improved penetration of the inhaled composition to its target site, which includes the small airways (bronchioles and alveoli), may be obtained by:
(i) Giving a higher dose-rate of the inhaled composition in order to achieve the wanted effect.
(ii) Applying continuous positive airway pressure (CPAP) with spontaneous breathing or extrinsic positive end-expiratory pressure (PEEP) in mechanical ventilation in order to facilitate the delivery of the inhaled preparation to the distal airways and enhance its effect.

The two applications of increased airway pressure (CPAP and PEEP) may increase the collateral ventilation (CV) via the ventilation pores between the terminal units of peripheral airways. The phenomenon of CV can be particularly useful in pulmonary disease with anatomical partial or total block of the airways, since it can increase delivery of drugs to the site of interest, which is the peripheral airways. By exploiting the occurrence of CV, CPAP and PEEP may cause air to bypass obstructed airways through collateral channels including interalveolar pores, bronchiole-alveolar communications, and interbronchiolar pathways. Resistance through these channels located at the small airways increases with decreasing lung volume. Functional blockage of the airways to the passage of an aerosol may thus be alleviated by exploiting the occurrence of CV, which facilitates the distribution of the compound into the airways beyond the level of obstruction. Thus, in one embodiment of the present invention, the compound is administered by inhalation combined with collateral ventilation, such as CPAP and/or PEEP.

Indications
1. Radiation to the chest region, e.g. in the form of radiotherapy for breast cancer, primary and secondary lung cancer and mediastinal irradiation for Hodgkin's disease.
2. Imminent radiation to the chest region from an expected nuclear event, e.g. to protect troops and civilians, especially by means of a pocket-size inhalation device for self-medication.
3. Radiation to the chest region from background radioactivity due to a nuclear event, especially by means of a pocket-size inhalation device for self-medication.
4. Cancer chemotherapy with one or more cytotoxic agents that may cause lung injury due to or exacerbated by cancer chemotherapy.

Dose and Dosage Regimens

By "effective amount" of the pharmaceutical compositions of the present invention is meant a dose, which, when administered to a subject in need thereof, achieves a concentration which has a beneficial biological effect, i.e. by preventing radiation or cytotoxic injury to the lungs. Such an effective amount may be determined physicians of ordinary skill in the art attending patients undergoing radiotherapy to the chest region or chemotherapy with agents that can cause lung damage.

The effective amounts and dosages of the ingredients of the composition are determined in relation to body weight or body surface area, though the relationship of lung surface area to be treated by airways administration to body weight or body surface area will vary between individual patients.

The effective amount of melatonin or a metabolite, derivative or analogue thereof for airways administration may be from 15 microgram (µg) to 300 µg per kilogram of body weight per dose, such as in the range of 30 µg to 200 µg per kilogram per day, and especially in the range of 75 µg to 150 µg per kilogram per dose. In terms of standard adult doses that do not take deviations of body weight into account, such standard doses may be from 1 mg to 20 mg, such as in the range of 2 mg to 15 mg, and especially in the range of 5 mg to 10 mg.

The effective amount of the pharmaceutically acceptable forms of vitamin E, coenzyme Q10, alpha-lipoic acid and vitamin C in admixture with melatonin or a metabolite, derivative or analogue thereof, may be the same by weight as the amount of melatonin or metabolite, derivative or analogue thereof.

In the case of radiotherapy to the chest region, the effective dose is preferably administered immediately before each dose of radiation is given. Because melatonin may also have longer term anti-inflammatory effects that are not directly dependent on free radical scavenging, the effective dose may also be given up to daily between and after doses of radiation for a period of up to 6 months after the initiation of radiotherapy. The daily dose may be given once a day or in divided or full effective doses two times a day, three times a day, four times a day, five times a day, or six times a day. The total daily dose may thus be from one to six times the amount of a single effective dose.

In case of an imminent nuclear event, the effective dose is preferably administered as soon as the immediate risk is established and repeated at two-hourly intervals until the event occurs or the risk is abated. Following a nuclear event or in the presence of background radiation from a nuclear event, dosing is continued according to the criteria of the daily dosing schedule outlined above, adjusted in accordance with the intensity of the radiation.

In the case of chemotherapy with cytotoxic agents, the effective dose is preferably administered immediately before each dose of chemotherapy is administered. Because the cytotoxic therapy may have a continuing damaging action on the lung epithelium, a further effective dose may be given starting 2 hours after the initiation of administration of the cytotoxic drug, and this dose may be fractionated in up to six fractions given over the following 24 hours. The effective dose may also be given up to daily between and after doses of chemotherapy for a period of up to 6 months after the initiation of chemotherapy. The daily dose may be given once a day or in divided doses two times a day, three times a day, four times a day, five times a day, or six times a day.

Duration of dosing will typically range from 3 months to 6 months.

A dose regimen may alternate between periods of administration of the pharmaceutical composition according to the present invention and periods with no administration (a pause in treatment). A period with a pause of treatment in such a dose regime may last for 1 week to 2 weeks, or 2 weeks to 3 weeks, or 3 weeks to 1 month, or 1 month to two months, all at the discretion of the attending physician.

Embodiments

1. A composition comprising melatonin or an antioxidant metabolite, derivative or analogue thereof formulated for administration via the airway to the epithelium of the lower airways for the prevention and treatment of lung damage due to chest irradiation and/or the administration of cytotoxic drugs.
2. A composition according to embodiment 1, comprising additionally a pharmaceutically acceptable form or derivative or analogue of one or more of the substances vitamin E, coenzyme Q10, alpha-lipoic acid and vitamin C.
3. A composition according to embodiments 1 or 2 for the prevention and treatment of lung damage due to chest irradiation.
4. A composition according to embodiments 1 or 2 for the prevention and treatment of lung damage due to cytotoxic chemotherapy.
5. A composition according to embodiments 1 or 2 for the prevention and treatment of lung damage due to a combination of chest irradiation and cytotoxic chemotherapy.
6. A composition according to embodiments 4 or 5, wherein the chemotherapy comprises any one of Bleomycin, or mitomycin C, or bis-chloroethylnitrosourea (BCNU or carmustine), or cyclophosphamide, or busulfan, or methotrexate, or doxorubicin, or gemcitabine, or paclitaxel, or docetaxel or carboplatins.
7. A composition according to embodiment 3 in which the chest irradiation is due to a nuclear event or to background radiation following a nuclear event.
8. The composition according to any one of the preceding embodiments formulated for administration via the airways by inhalation or by intratracheal, intrabronchial or intralveolar administration.
9. The composition according to any one of the preceding embodiments, wherein the composition is for inhalation as a powder.
10. The composition according to embodiments 1 to 8, wherein the composition is for inhalation as an aerosol.
11. the composition according to any one of embodiments 9 or 10, wherein the composition is made for delivery using any one of a Dry powder inhaler system (DPI) or a Pressurized nebulizer using compressed air/oxygen mixture, or an Ultrasonic nebulizer, or an Electronic micropump nebulizer (e.g. Aeroneb Professional Nebulizer), or a Metered dose inhaler (MDI).
12. The composition according to any one of the preceding embodiments, wherein the composition is for administration 1, 2, 3, 4, 5, or 6 times per day.
13. The composition according to any one of the preceding embodiments, wherein the composition is for administration over a period of up to 3 months or more, such as 4 months or more, such as 5 months or more, such as 6 months or more.
14. The composition according to any one of the preceding embodiments, wherein the single dose of melatonin or metabolite, derivative or analogue thereof is from 15 µg to 300 µg per kilogram of body weight per day, such as in the range of 30 µg to 200 µg per kilogram of body weight per day, and especially in the range of 75 µg to 150 µg per kilogram of body weight per day.
15. The composition according to embodiments 1 to 12, wherein the single standard adult dose of melatonin or metabolite, derivative or analogue thereof is 1 mg to 20 mg, such as in the range of 2 mg to 15 mg, and especially in the range of 5 mg to 10 mg.
16. The composition according to any one of the preceding embodiments, wherein the daily dose of melatonin is from one to six times the single doses of embodiments 14 and 15.
17. The composition according to any one of the preceding embodiments, wherein a single dose of melatonin or metabolite, derivative or analogue thereof is administered immediately before an episode of irradiation or a dose of chemotherapy.
18. The composition according to any one of the preceding embodiments, wherein a single dose of melatonin or metabolite, derivative or analogue thereof is administered immediately before an episode of irradiation or a dose of chemotherapy, wherein the dose of chemotherapy comprises any one of Bleomycin, or mitomycin C, or bis-chloroethylnitrosourea (BCNU or carmustine), or cyclophosphamide, or busulfan, or methotrexate, or doxorubicin, or gemcitabine, or paclitaxel, or docetaxel or carboplatins.
19. The composition according to any one of the preceding embodiments, wherein the composition is made for administration in combination to systemic or oral treatment with melatonin or another antioxidant.
20. The compositions of anyone of the above embodiments, for use in a method of treatment.

Example 1: Clinical Trial of the Effect of Inhaled Melatonin to Prevent or Ameliorate Radiation Pneumonitis Patients aged 18 years or more are recruited into the clinical trial when a clinical decision has been made to treat a primary or secondary cancer of the chest with external beam radiotherapy with a total radiation dose in the range of 2-70 Gy that because of the location of the tumor(s) will impinge on the lungs. Once the patients have given informed, written consent, they undergo baseline clinical and paraclinical assessment of their pulmonary status and are then randomized to receive either a melatonin or a placebo inhalation immediately before each fraction of radiotherapy is given and every night before retiring.

Between 10 and 20 patients are allocated to each of the melatonin (treatment) and placebo groups.

The clinical and paraclinical assessment includes at least the following: a questionnaire to record subjective symptoms and self-assessment of cough, shortness of breath, wheeze, sputum production, chest pain and exercise tolerance; standard pulmonary function tests including FEV1 (forced expiratory volume in the first second) and FVC (forced vital capacity); antero-posterior and lateral chest x-ray films. Blood is taken for routine hematological and biochemical tests, and serum and plasma samples are stored frozen for post-hoc analysis of inflammatory markers such as IL-6.

Patients are taught to self-administer the inhalation of an aerosol of melatonin or inert placebo. The method of administration is chosen from those described and will preferably be by inhalation of a micronized powder through a hand-held device. The dosage of melatonin is in the range of 5-20 mg per inhalation. The inhalation is administered no more than 15 minutes before the start of delivery of each fraction of radiation. The dose is repeated each night on retiring.

The clinical and paraclinical assessment described above is repeated at 4-week intervals for at least 12 weeks. Any lung infections occurring within the period are investigated and recorded.

At the conclusion of the trial, the results are analyzed to assess whether the treatment has had a significant effect to prevent or ameliorate the symptoms and signs of radiation pneumonitis.

REFERENCES

Gomez-Moreno G, Guardia J, Ferrera M J, Cutando A, Reiter R J (2010) Melatonin in diseases of the oral cavity. Oral Dis 16:242-247.

Hashimura T, Kono M, Imajo Y (1989) [Experimental studies on mechanisms and prevention of radiation pneumonitis] [Article in Japanese]. Nihon Igaku Hoshasen Gakkai Zasshi (J Japanese Radiol Soc) 49:335-343.

Maharaj D S, Glass B D, Daya S (2007) Melatonin: new places in therapy. Biosci Rep 27:299-320.

Movsas B, Raffin T A, Epstein A H, Link C J Jr (1997) Pulmonary radiation injury. Chest 111:1061-1076.

Oxenkrug G (2005) Antioxidant effects of N-acetylserotonin: possible mechanisms and clinical implications. Ann N Y Acad Sci 1053:334-347.

Reiter R J, Tan D X, Terron M P, Flores L J, Czarnocki Z (2007) Melatonin and its metabolites: new findings regarding their production and their radical scavenging actions. Acta Biochim Pol 54:1-9.

Rodriguez C, Mayo J C, Sainz R M, Antolin I, Herrera F, Martin V, Reiter R J (2004) Regulation of antioxidant enzymes: a significant role for melatonin. J Pineal Res 36:1-9.

Tan D X, Chen L D, Poeggeler B, Manchester L C, Reiter R J (1993) Melatonin: a potent, endogenous hydroxyl radical scavenger. Endocrine J 1:57-60.

Vijayalaxmi, Reiter R J, Herman T S, Meltz M L (1996) Melatonin and radioprotection from genetic damage: in vivo/in vitro studies with human volunteers. Mutat Res 371:221-228.

Vijayalaxmi, Reiter R J, Tan D X, Herman T S, Thomas C R Jr (2004) Melatonin as a radioprotective agent: a review. Int J Radiat Oncol Biol Phys 59:639-653.

The invention claimed is:

1. A method for the treatment of lung damage due to chest irradiation, said method comprising:

providing a composition comprising a micronized powder, which comprises melatonin, to a patient, wherein:

said patient is selected as having a primary or secondary cancer of the chest and is to receive external beam radiotherapy with a total radiation dose in the range of 2-70 GY;

said selected patient receives said composition via intratracheal, intrabronchial, or bronchoalveolar inhalation no more than 15 minutes before each dose of said radiotherapy;

said micronized powder comprises a sugar excipient and particles having an aerodynamic diameter of 2 μm to 5 μm; and the dosage of melatonin administered is in the range of 5-20 mg per inhalation.

2. The method of treatment according to claim 1, wherein the sugar excipient is lactose, mannitol, or xylitol.

3. The method according to claim 1, wherein the composition is administered 1, 2, 3, 4, 5, or 6 times per day.

4. The method according to claim 1, wherein the composition is administered over a period of up to 3 months or more.

5. The method according to claim 1, wherein a single dose of the composition administered comprises a dose of melatonin of 15 μg to 300 μg per kilogram of body weight.

6. The method according to claim 1, wherein the single standard adult dose of melatonin is 1 mg to 20 mg.

7. The method according to claim 1, wherein the total daily dose of melatonin is from one to six times the single dose of 15 μg to 300 μg per kilogram of body weight.

8. The method according to claim 1, wherein a single dose of melatonin is administered immediately before an episode of irradiation and each night before retiring.

* * * * *

UNITED STATES PATENT AND TRADEMARK OFFICE
CERTIFICATE OF CORRECTION

PATENT NO. : 11,903,925 B2
APPLICATION NO. : 16/162222
DATED : February 20, 2024
INVENTOR(S) : Lars Otto Uttenthal It is certified that error appears in the above-identified patent and that said Letters Patent is hereby corrected as shown below:

In the Specification

Column 3, Line 17, delete "emotive" and insert -- emptive --.

Column 4, Line 39, delete "(AMMO)" and insert -- (AMMC) --.

Column 9, Line 27, delete "(DPI)." and insert -- (DPI) --.

Column 12, Line 1, delete "11. the" and insert -- 11. The --.

Signed and Sealed this
Twenty-eighth Day of May, 2024

Katherine Kelly Vidal
*Director of the United States Patent and Trademark Office*